US012685564B1

(12) United States Patent
Bronder, Jr.

(10) Patent No.: US 12,685,564 B1
(45) Date of Patent: Jul. 21, 2026

(54) SPINAL TRACTION DEVICE AND METHOD

(71) Applicant: Charles J. Bronder, Jr., Hypoluxo, FL (US)

(72) Inventor: Charles J. Bronder, Jr., Hypoluxo, FL (US)

( * ) Notice: Subject to any disclaimer, the term of this patent is extended or adjusted under 35 U.S.C. 154(b) by 144 days.

(21) Appl. No.: 18/476,469

(22) Filed: Sep. 28, 2023

Related U.S. Application Data

(60) Provisional application No. 63/413,275, filed on Oct. 5, 2022.

(51) Int. Cl.
*A61B 17/64* (2006.01)
(52) U.S. Cl.
CPC ...... *A61B 17/6433* (2013.01); *A61B 2560/02* (2013.01)
(58) Field of Classification Search
CPC .. A61H 1/0218; A61H 1/0222; A61H 1/0292; A61H 1/0296; A61F 5/05883; A61F 5/05891
See application file for complete search history.

(56) References Cited

U.S. PATENT DOCUMENTS

| | | | | |
|---|---|---|---|---|
| 1,837,153 A | * | 12/1931 | Ettinger | A61H 1/0218 602/17 |
| 2,674,996 A | | 4/1954 | Stowell et al. | |
| 2,851,031 A | * | 9/1958 | Ciampa | A61H 1/0218 602/17 |
| 4,987,886 A | | 1/1991 | McDonald et al. | |
| 5,109,835 A | * | 5/1992 | McDonald | A61F 5/055 602/17 |
| 5,451,202 A | | 9/1995 | Miller et al. | |
| 6,875,189 B1 | | 4/2005 | Nelson | |
| 11,083,663 B1 | | 8/2021 | Mullins | |
| 2004/0204666 A1 | | 10/2004 | Marsh | |
| 2013/0226055 A1 | * | 8/2013 | Akpotaire | A61F 5/055 602/18 |
| 2019/0351172 A1 | | 11/2019 | Formica et al. | |

FOREIGN PATENT DOCUMENTS

WO          2015040255 A1     3/2015

* cited by examiner

*Primary Examiner* — Kari K Rodriquez
(74) *Attorney, Agent, or Firm* — John Rizvi; John Rizvi, P.A.—The Patent Professor ®

(57) ABSTRACT

A spinal traction device, mountable on a head of a wearer for the application of a traction force, includes a front piece arrangeable in front of the face of the wearer. Top and bottom fasteners may extend from the front piece and secure to a top and a bottom of the head, respectively. A rear portion of the bottom fastener may be arranged below the occiput of the head. First and second elongate members may extend from opposite sides of the bottom fastener in a generally axial direction relative to the wearer's spine. An axial, traction force may be applied by the rear portion of the bottom fastener on the occiput by exerting an axial pulling force on the first and second elongate members, allowing a spine traction to be performed with the spine in a neutral position and the head and neck in various positions.

13 Claims, 13 Drawing Sheets

SPINAL TRACTION DEVICE AND METHOD

CROSS-REFERENCE TO RELATED APPLICATION

This application claims the benefit of U.S. Provisional Patent Application No. 63/413,275, filed on Oct. 5, 2022, which is incorporated herein by reference in its entirety.

FIELD OF THE INVENTION

The present invention relates generally to spinal traction devices, and more particularly, to a spinal traction device mountable to a subject's head to facilitate spinal traction in a vertical or axial direction with increased comfort to the subject, and with the head and neck positionable in various positions enabling complete/full dynamic patterns of movement/mobility (flexion, extension, side bending, and rotation) performed during all phases of axial distractive force applications.

BACKGROUND OF THE INVENTION

Spinal compression is a common medical condition in adult humans, by which the vertebrae and discs forming the vertebral column or spine are compressed towards one another. A person suffering from spinal compression may feel pain, numbness, or weakness in the arms, lands, legs, or feet. Prolonged or severe spinal compression may evolve into more serious medical conditions such as bone fracture, sciatica, herniated disc, chronic muscle contracture, etc.

Common causes of spinal compression are, for instance, poor body posture, insufficient or excessive physical activity, stress, muscle contractures, or aging. The most prevalent form of spinal and nerve root compression arises secondary to degenerative disc changes (dehydration and disc shrinkage which results in slippage of the vertebrae in a compression plane which causes misalignment and compression upon the thecal sac, reducing spinal fluid circulation and compression upon the spinal cord and nerve roots.

Treatment of spinal compression typically seeks to stretch the spine, or increase the separation between the vertebrae forming the spine. One example of a spinal stretching technique consists in a cervical traction, by which a light pulling force is applied on the subject's head in order to stretch the cervical section of the spine, i.e. the upper area of the spine corresponding generally to the subject's neck. Cervical traction is typically carried out by a healthcare provider such as, but not limited to, a chiropractor or physical therapist. In some cases, the subject may perform cervical traction on his or herself, such as at their home.

In professional settings, cervical traction is typically carried out using a traction or pulling apparatus, which may include a harness attachable to the subject's head and a pulling machine configured to exert a traction or pulling force on the harness. By pulling on the harness, a pulling force is exerted on the subject's head generally away from the body, thereby stretching the cervical section of the spine.

In conventional harnesses, prior to conducting the cervical traction, the subject or patient is typically positioned with their neck resting on a structure which flexes the neck, and thus the spine, to a non-neutral position. For instance, the structure may be sloped or wedge-shaped. Thus, the cervical traction treatment is necessarily carried out with the head in the flexed position, and cannot be carried out with the head in alternative positions (which could be medically beneficial in some cases).

Furthermore, when using conventional harnesses, the cervical traction force applied on the subject's spine may be arranged along a slightly oblique direction relative to an axial or neutral direction of the subject's body, i.e. relative to a generally vertical direction when the subject is standing or to a generally horizontal direction when the subject is lying on a horizontal surface. Specifically, the traction force is directed from the occiput or back of the head towards the forehead. This may result in the upper neck being tilted forward into extension, and subsequently being extended while flexed forward. This often causes the head to slip out of the harness when the traction force exceeds a certain threshold, which is often equal to the weight of the subject's head. Clearly, having a subject's head slip out of a traction harness may cause further damage to the subject's spine and other body parts, as well as diminish the subject's comfort during the cervical traction procedure and overall confidence in the cervical traction technique.

Accordingly, there remains a need in the art to at least one of the aforementioned problems. For example, there is an established need for a spine traction apparatus configured to apply a traction on a subject's spine in an axial direction, i.e. with the spine in a neutral position, and allowing the subject's head to be positioned in any given orientation, such as extended or flexed forward or in any other applicable position.

SUMMARY OF THE INVENTION

The present invention is directed to a spinal traction device and method configured for the exertion of traction or pulling forces on a subject's head in a generally axial direction. The spinal traction device allows the subject to comfortably and safely maintain their head in a non-extended or flexed position, or any other applicable position, during a spinal traction procedure. The invention enables complete/full dynamic patterns of movement/mobility (flexion, extension, side bending, and rotation) performed during all phases (minimum and maximum) of axial distractive force applications.

In a first implementation of the invention, a spinal traction device, mountable on a head of a wearer and configured to exert a traction force on the head of the wearer, may include a front piece, arrangeable in front of the face of the wearer. The spinal traction device may further include a fastener assembly, attachable to and extendable from the front piece to form a loop together with the front piece, the loop configured to extend around the head of the wearer. The spinal traction device may additionally include first and second connecting members carried by the fastener assembly. The spinal traction device may be configured to adopt a working configuration in which the fastener assembly is attached to and extends from the front piece such that the front piece and fastener assembly form said loop, wherein the loop is arranged about the head of the wearer; the front piece may be arranged in front of the face of the wearer and the fastener assembly wrapped around the back of the head of the wearer such that a rear portion of the fastener assembly is arranged adjacent to an inwardly-directed surface of an occiput of the head and is aligned with the inwardly-directed surface in an axial direction of a spine of the wearer. Also in the working configuration, the first and second connecting members may be arranged at opposite sides of the spinal traction device arranged, in turn, at opposite left and right sides of the head, respectively. Furthermore, a traction force applied on the first and second connecting members, the traction force having an axial component, may be transferred by the fastener assembly to said rear portion of the fastener assembly and a resulting traction force having an axial component may be applied to said inwardly-directed surface of the occiput of the head by said rear portion of the fastener assembly abutting against the inwardly-directed surface of the occiput.

These and other objects, features, and advantages of the present invention will become more readily apparent from the attached drawings and the detailed description of the preferred embodiments, which follow.

BRIEF DESCRIPTION OF THE DRAWINGS

The preferred embodiments of the invention will hereinafter be described in conjunction with the appended drawings provided to illustrate and not to limit the invention, where like designations denote like elements, and in which.

Like reference numerals refer to like parts throughout the several views of the drawings.

DETAILED DESCRIPTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

The present invention is directed to a spinal traction device and method configured for the exertion of traction or pulling forces on a subject's head in a generally axial direction. The spinal traction device allows the subject to comfortably and safely maintain their head in a non-extended or flexed position or any other applicable position during the spinal traction procedure.

Figure 1:
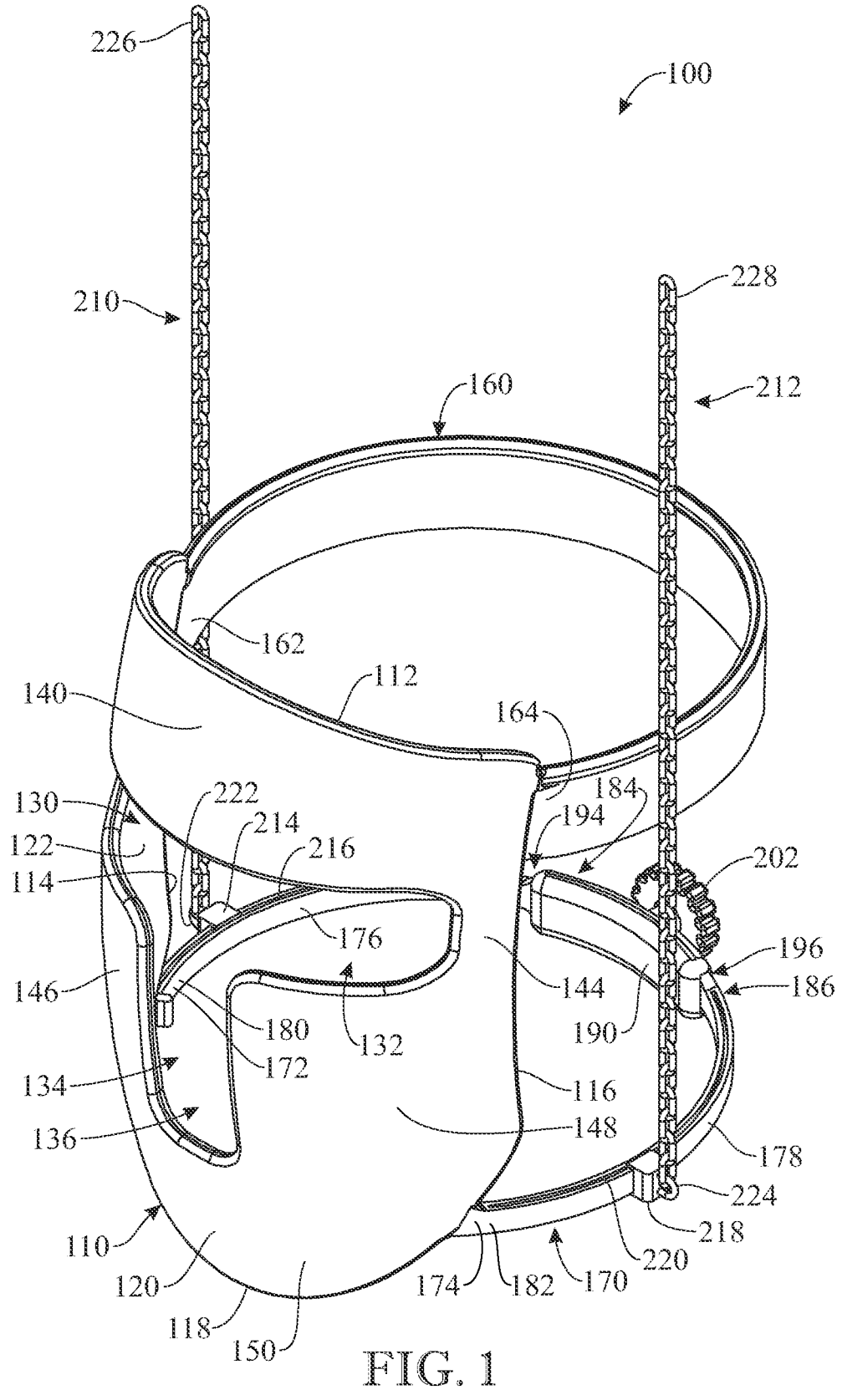
FIG. 1 presents a top, front isometric view of a spinal traction device in accordance with an illustrative embodiment of the present invention, the spinal traction device shown with top and bottom fasteners looped and with first and second elongate members slidably secured to the bottom fastener at opposite sides thereof and extending over the top fastener.
Figure 2:
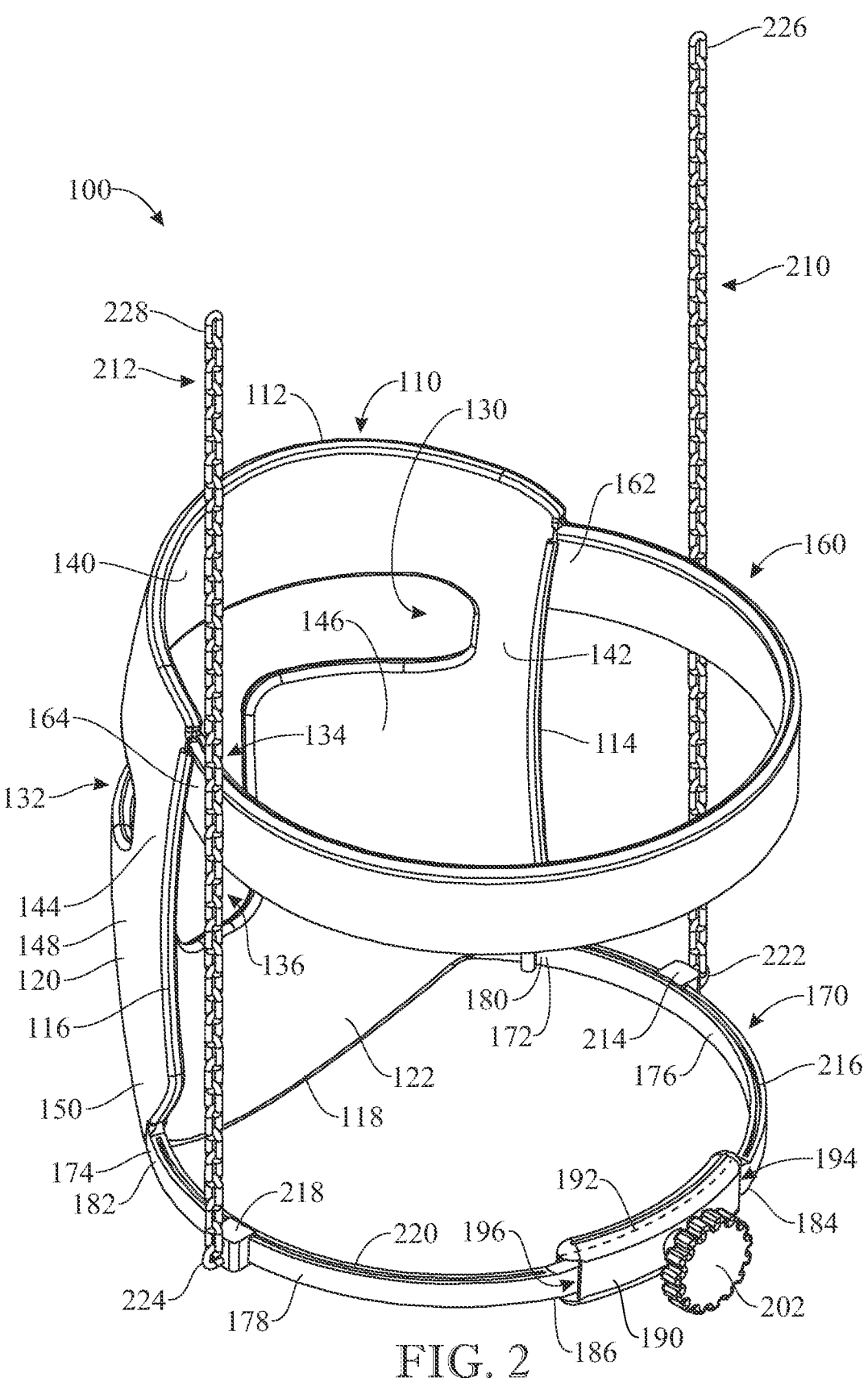
FIG. 2 presents a top, rear isometric view of the spinal traction device of FIG. 1.
Figure 3:
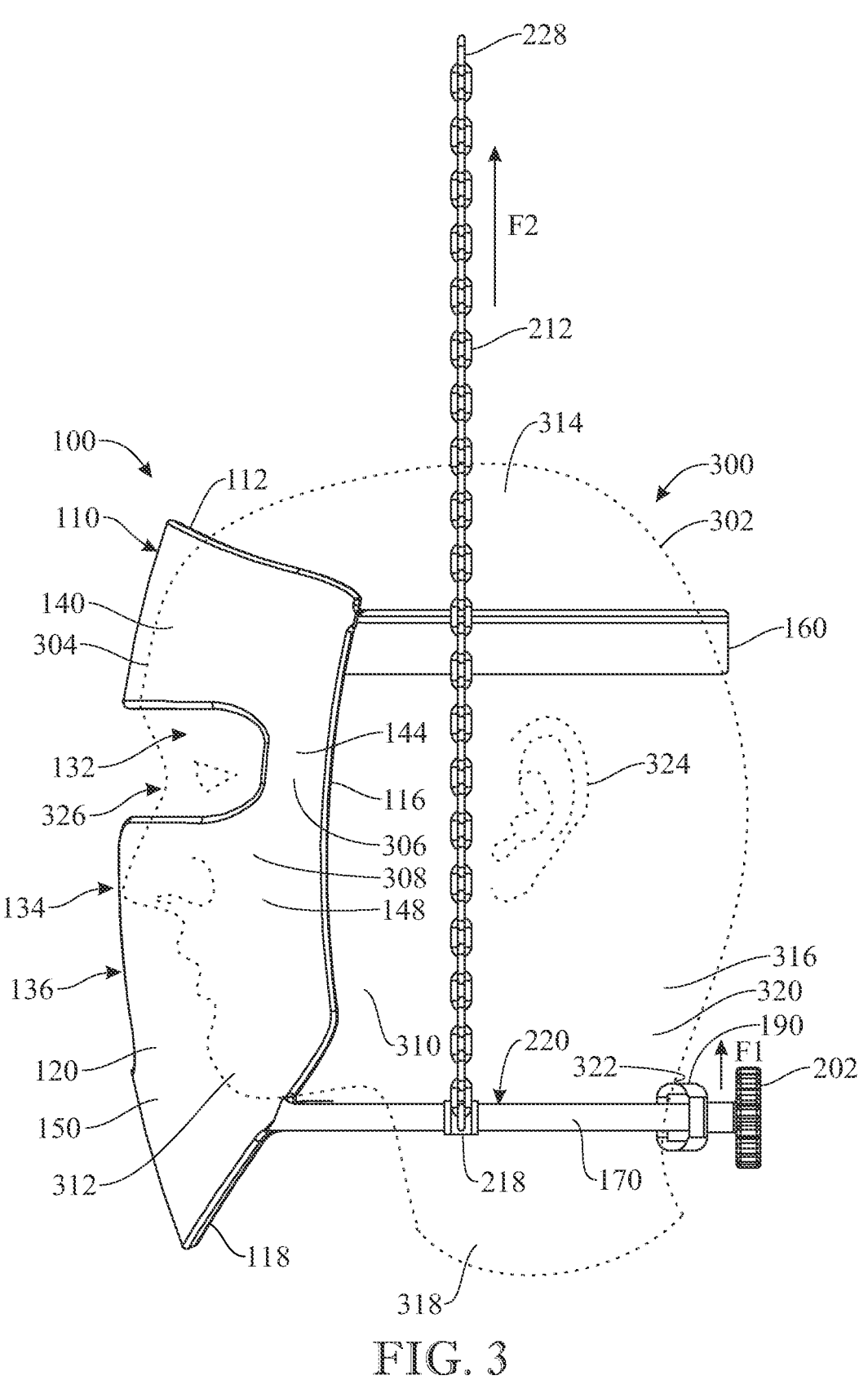
FIG. 3 presents a side elevation view of the spinal traction device of FIG. 1, showing the device fitted onto a wearer's head, and further depicting the operation of the device with the side, first and second elongate members arranged in a neutral or axial direction and a traction force being applied in the axial direction on the mask and the wearer's head.

Referring initially to FIGS. 1-3, a spinal traction device 100 mountable to a head 302 of a subject or wearer 300 (FIG. 3) is illustrated in accordance with an embodiment of the invention. The spinal traction device 100 may include a front piece 110 arrangeable at a front area of the subject's head. For instance and without limitation, the front piece 110 may be arrangeable to at least partially cover the subject's face, as in the present embodiment, such that the front piece constitutes a face mask. In preferred embodiments, the front piece 110 is generally rigid and undeformable; for instance and without limitation, the front piece 110 may be made of plastic, a thick leather or stack of leather sheets, or combinations thereof. In some embodiments, the front piece 110 may be custom-printed (e.g., 3D-printed), molded, or otherwise customized based on the outer shape and contour of the face of each specific wearer.

In some embodiments, such as the present embodiment, the front piece 110 may include a top edge 112, and two opposite, left and right side edges 114 and 116, respectively, extending from opposite left and right ends of the top edge 112. A bottom edge 118 may extend from respective bottom ends of the left and right side edges 114, 116. In some embodiments, the top edge 112 and left and right side edges 114, 116 may be generally straight; for example, the top edge 112 of the present embodiment is curved outward only slightly, and the left and right side edges 114, 116 are only slightly curved inward. The bottom edge 118, in turn, may be more prominently curved or angled downward to accommodate at least part of the contour of the subject's jaw and chin, as shown; for instance and without limitation, the bottom edge 118 may be U-shaped (as shown), V-shaped, or otherwise downward protruding. Alternative embodiments are contemplated regarding the front piece 110, however, without departing from the scope of the present disclosure.

As best shown in FIGS. 1 and 2, the front piece 110 may have a front side 120 and a rear side 122, configured to be oriented away from and towards the subject's face, respectively, when the spinal traction device 100 is mounted on the subject's head. In some embodiments, the front and rear sides 120 and 122 may be generally parallel to one another. Alternatively or additionally, the front piece 110 may be curved or otherwise non-flatly formed to conform to the subject's face to some extent. For example, the front piece 110 of the present embodiment has both parallel front and rear sides 120 and 122, and a non-planar shape configured to wrap around and conform to the subject's face. In some embodiments, the rear side 122 may be configured to provide a pleasant and non-irritant touch against the subject's skin, in the event that the rear side 122 touches the user's skin. For example, the rear side 122 may be smooth, soft, and made of biocompatible materials.

In some embodiments, such as the present embodiment, the front piece 110 may include one or more of a left eye opening 130, a right eye opening 132, a nose opening 134, and a mouth opening 136, formed through the front piece 110, from the front side 120 to the rear side 122, and configured to align with the left eye, right eye, nose, and mouth of the subject wearing the spinal traction device 100. In some embodiments, the left and right eye openings 130 and 132 may be communicated with or extend from each other. Alternatively or additionally, the nose opening 134 may be communicated with or extend from one or both of the left and right eye openings 130 and 132. Alternatively or additionally, the nose opening 134 and the mouth opening 136 may be communicated with or extend from each other. For example, the present embodiment is provided with all such features; i.e., the left and right eye openings 130 and 132 are communicated with and extend from the nose opening 134, which in turn is communicated with and extends from the mouth opening 136. More specifically, in the depicted embodiment, said openings 130, 132, 134, 136 jointly form a T-shaped opening extending through the front piece 110, which may contribute to reducing manufacture cost (as the number of openings is minimal or relatively low) without adversely affecting user comfort. In some embodiments, such as the present embodiment, the front piece 110 may be generally solid, with the exception of the one or more aforementioned openings 130, 132, 134 and/or 136.

With continued reference to FIGS. 1 and 2, in some embodiments, the front piece 110 may include a forehead or top portion 140. The top portion 140 may extend between the top edge 112, a top end of the left and right side edges 114 and 116, and the one or more left and right eye openings 130, 132, and may be configured to align with the forehead 304 of the wearer 300. Left and right temple portions 142 and 144 may extend from the top portion 140 between the left eye opening 130 and the left side edge 114, and between the right eye opening 132 and the right side edge 116, respectively; the left and right temple portions 142 and 144 may be configured to align generally with the wearer's left and right temples 306. Left and right cheek portions 146 and 148 may extend from the left and right temple portions 142 and 144, at opposite sides of the nose opening 134, between the nose opening 134 and the left and right side edges 114 and 116, respectively; the left and right cheek portions 146 and 148 may be configured to align with the left and right cheeks 308 of the wearer 300. A bottom portion 150 may extend from the left and right cheek portions 146 and 148 to the bottom edge 118, and may be configured to align generally with the wearer's jaw 310 and chin 312. The top portion 140, left and right temple portions 142, 144, left and right cheek portions 146 and 148, and bottom portion 150 may extend continuously from one another and thereby enclose the T-shaped opening formed by the eye, nose and mouth openings 130, 132, 134, 136.

With reference to FIGS. 1-3, the spinal traction device 100 may further include at least one fastener configured to secure the front piece 110 to the wearer's head 302 such that the front piece 110 is generally immobilized relative to the head 302. Preferably, the at least one fastener secures the front piece 110 to the head at or near the top and bottom portions 140, 150 of the front piece 110. For example, the at least one fastener may include a top fastener 160, which may be attached to and extend from the top portion 140 of the front piece 110 and configured to wrap around and secure to the top 314 of the wearer's head 302, as shown in FIG. 3. In some embodiments, such as the present embodiment, opposite first and second ends 162 and 164 of the top fastener 160 may extend from the left and right side edges 114 and 116, respectively, at the top portion 140, and may form a loop with the top portion 140, the loop configured to wrap around the top 314 of the wearer's head 302. In some embodiments, the top fastener 160 may be made generally of plastic, leather, or other skin-compatible material.

Alternatively or additionally, the at least one fastener may include a bottom fastener 170, attached to and extending from the bottom portion 150 of the front piece 110 and configured to wrap around and secure to the bottom 316 of the wearer's head 302 (FIG. 3). In some embodiments, such as the present embodiment, opposite first and second ends 172 and 174 of the bottom fastener 170 may extend from opposite left and right ends of the bottom edge 118 and may form a loop with the bottom portion 150 of the front piece 110, the loop configured to wrap around the bottom 316 of the wearer's head 302. In some embodiments, the bottom fastener 170 may be made generally of plastic, leather, or other skin-compatible material.

In preferred embodiments, as shown in FIG. 3, the bottom fastener 170 may be configured to wrap around the bottom 316 of the wearer's head 302 (or top of the wearer's neck 318) and to abut against the wearer's occiput 320, in axial alignment with the occiput 320 (lower back area of the head 302) such that the bottom fastener 170, and more specifically, a retainer 190, may exert a generally axial force F1 on the wearer's occiput 320; for example, in the specific example shown in FIG. 3, the bottom fastener 170 may abut against an inward surface 322 of the occiput 320, the inward surface 322 oriented inward or otherwise toward the wearer's face 326, the inward surface 322 having a radial component which allows the bottom fastener 170 to exert a vertically upward or axial force F1 on the inward surface 322 of the occiput 320, to softly pull the head 302 away from the neck 318 in an axial direction and thereby stretch the spine with the head in a neutral position, as shown in FIG. 3. In some embodiments, such as the present embodiment, it is the retainer 190 of the bottom fastener 170 that abuts against and exerts said force on the occiput 320, and more specifically, the inward surface 322 of the occiput 320. In a preferred embodiment, the retainer 190 may be made of or include a soft material or cushioning (e.g., soft plastic, rubber, silicone, etc.) to provide a comfortable pressing and pushing on the occiput 320.

In some embodiments, the top fastener 160 may be flexible and deformable, which may provide increased comfort to the wearer 300. For example, the top fastener 160 may be a strap, which may be made of nylon or other flexible materials or combinations thereof. In some embodiments, when the top fastener 160 is looped, wrapped, or extended around the top 314 of the wearer's head 302, the top fastener 160 may adjust against the top 314 of the wearer's head 302. For instance, in some embodiments, the top fastener 160 may be length-adjustable, such as by having a strap-type top fastener 160 divided into two strap portions which are adjustably securable, such as by a hook-and-loop or other disconnectable and adjustable fastener, at different relative overlapping positions to selectively adjust a size of the loop formed around the top 314 of the head 302. In another example, the top fastener 160 may be elastically stretchable such that, when looped or wrapped around the top 314 of the head 302, the top fastener 160 may be elastically biased to compress and adjust against the top 314.

The top and bottom fasteners 160 and 170 may be arranged in spaced-part configuration. In some embodiments, the bottom fastener 170 may be more rigid, or less flexible, than the top fastener 160; more preferably, the bottom fastener 170 may be generally rigid or non-flexible. As shown in FIG. 3, the bottom fastener 170 may be configured to extend around the bottom 316 of the wearer's head 302 without rubbing or abutting against the head 302 except at the occiput 320 as heretofore described. I.e., in such embodiments, the bottom fastener 170 may be deployable to extend around and in spaced-apart relationship with the wearer's head 302, including the neck 318, and to contact the wearer 300 only at the occiput 320 for the application thereon of force F1 as heretofore described.

In certain embodiments, the bottom fastener 170 may be selectively adjustable to vary the size of the loop formed by the bottom fastener 170 and the front piece 110. For instance, as best shown in FIG. 2, in some embodiments, such as the present embodiment, the bottom fastener 170 may include a first elongated portion or segment 176 and a second elongated portion or segment 178 extending from the front piece 110. The first and second ends 172 and 174 of the bottom fastener 170 may be located at respective first ends 180 and 182 of the first and second segments 176 and 178. In turn, opposite, second ends 184 and 186 of the first and second segments 176 and 178 may be selectively adjustable relative to one another in different overlapping relationships allowing to vary the overall size of the loop.

Figure 6:
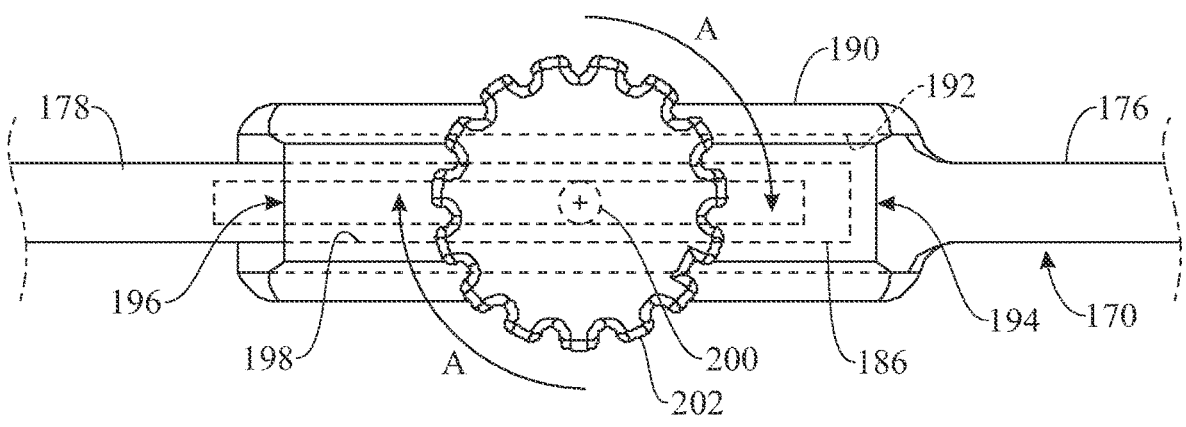
FIG. 6 presents an enlarged, rear elevation view of the retainer and adjustment knob enabling a selective adjustment of the overlapping of first and second segments of the bottom fastener, to vary the size of the looped, bottom fastener.
Figure 7:
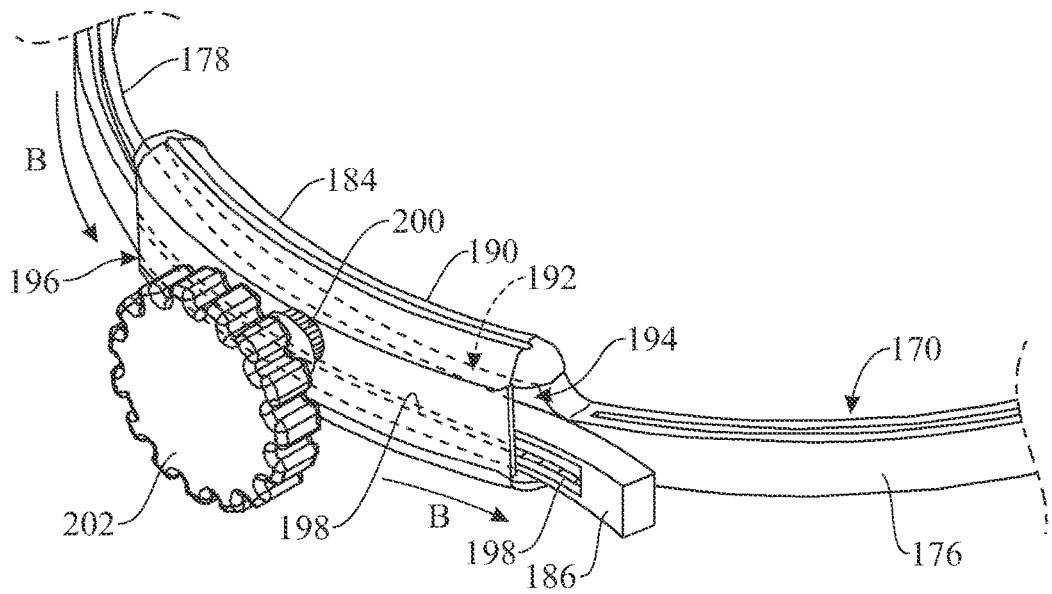
FIG. 7 presents a top, rear isometric view of the retainer and adjustment knob of FIG. 6, showing operation of a rack and pinion mechanism to selectively adjust the overlapping of the first and second segments of the bottom fastener.

In the depicted, non-limiting example, the first segment 176 comprises the retainer 190 at the second end 184. The retainer 190 may be integrally formed or otherwise attached to the remainder of the first segment 176, and may include a channel 192 formed therealong. For example, the retainer 190 may be formed as a generally hollow tube or sleeve, with the channel 192 formed through the retainer 190 from a first end opening 194 of the retainer 190 to an opposite, second end opening 196 of the retainer 190. As shown in FIGS. 6 and 7, the second end 186 of the second segment 178 may slidably extend through the second end opening 196 and the channel 192; in some embodiments, the bottom fastener 170 may be sufficiently tightened such that the second segment 178 extends outward through the first end opening 194 and outward of the channel 192, as shown in FIG. 7. The second segment 178 may include a rack 198, formed along at least part of the second segment 178. A pinion 200 may be carried by the first segment 176, and more specifically, by the retainer 190, and may be operationally engaged with the rack 198 of the second segment

178. A user-operable knob 202 may be attached to and jointly rotatable with the pinion 200. The knob 202 may be rotatably carried by the first segment 176, and more specifically, by the retainer 190, such that a manual rotation of the knob 202 and thus the pinion 200 in a first direction, indicated by arrow A (FIG. 6), causes the rack 198, and thus the second segment 178, to further overlap with the first segment 176 as indicated by arrows B (FIG. 7), thereby reducing the size of the loop formed by the first and second segments 176 and 178. Inverse operation of the knob 202, i.e. in a direction opposite to arrows A (FIG. 6) may in turn cause the second segment 178 to retract in a direction opposite to arrows B (FIG. 7) to reduce the overlapping of the first and second segments 176 and 178 and thus increase the size of the loop formed by the first and second segments 176 and 178. In this way, by manually rotating the rack and pinion mechanism via the user-operable knob 202, the size of the loop formed by the first and second segments 176 and 178 and the front piece 110 may be adjusted.

Referring again to FIGS. 1 and 2, the spinal traction device 100 may further include elongate, first and second connecting members, hereinafter referred to as first elongate member 210 and second elongate member 212. The first and second elongate members 210 and 212 may be configured for the pulling thereon by an external apparatus (not shown), as indicated by arrow F2 (FIG. 3), and to transfer this pulling or traction force to the occiput 320, i.e. to convert the pulling force by the external apparatus to the aforementioned pulling force F1 on the occiput 320. In some embodiments, such as the present embodiment, the first and second elongate members 210, 212 may be flexible; for instance and without limitation, the first and second elongate members 210, 212 may include a chain (as shown), cord, strap, band, etc. In some embodiments, such as the present embodiment, the first and second elongate members 210, 212 may be axially non-stretchable, to maximize the transfer of forces from the pulling action (force F2) to the occiput 320 (force F1). By 'axially non-stretchable', it is understood that a length of the first and second elongate members 210, 212 does not increase as a result of a pulling force (e.g., force F2) thereon once the first and second elongate members 210, 212 are extended to a generally straight position, shown in the drawings.

Figure 4:
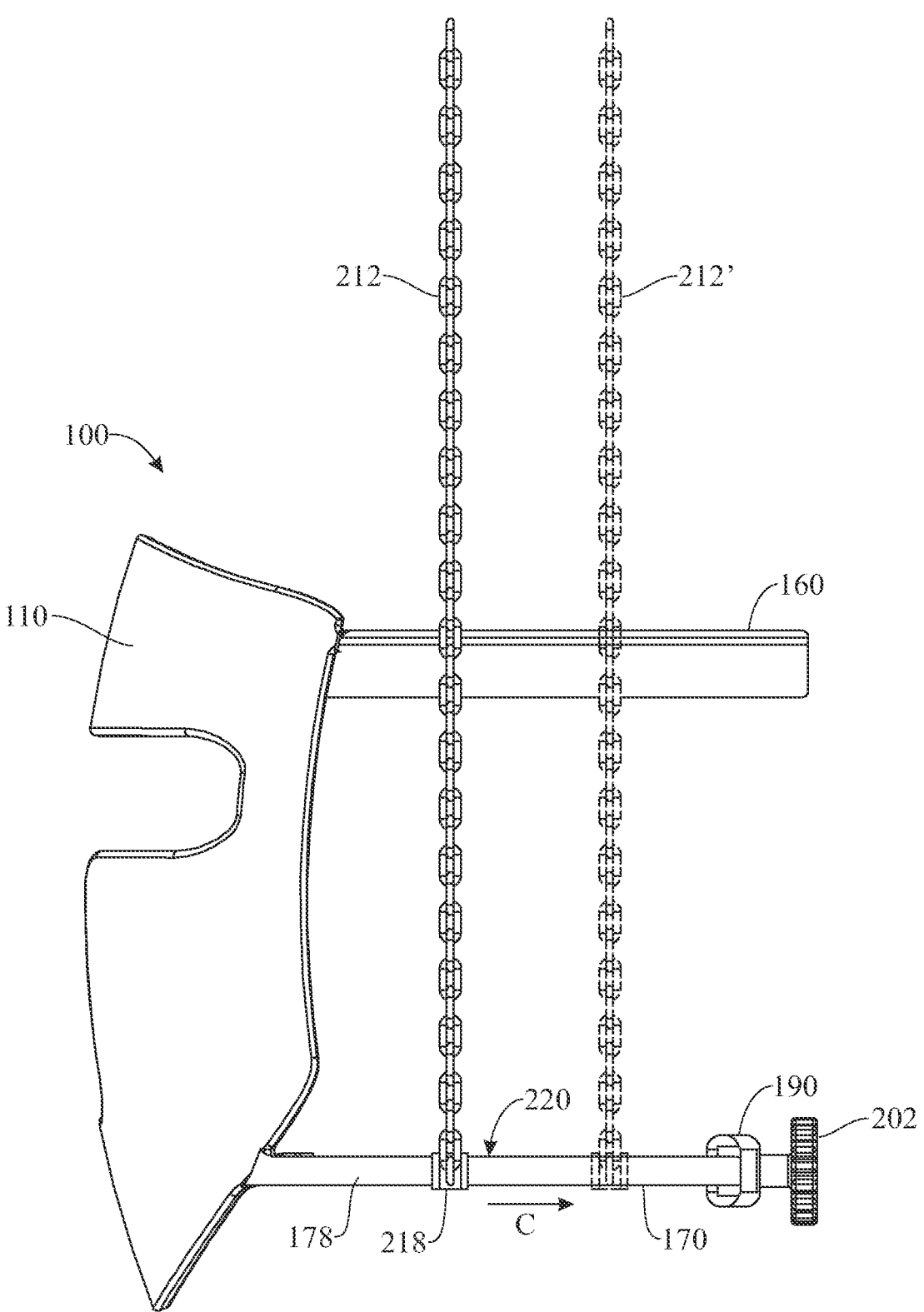
FIG. 4 presents a side elevation view, similar to FIG. 3, illustrating a slidable adjustment of the second elongate member along the bottom fastener.

In some embodiments, at least one of the first and second elongate members 210 and 212 may be secured to the bottom fastener 170, and further optionally slidably secured to the bottom fastener 170, enabling a selective repositioning thereof along the bottom fastener 170. For instance, in the present embodiment, both the first and second elongate members 210 and 212 are slidably secured to the bottom fastener 170 at opposite sides thereof. More specifically, the first elongate member 210 is connected to a bracket 214, which is in turn slidably coupled with and slidable along a track 216 formed into and along the first segment 176 of the bottom fastener 170. Similarly, the second elongate member 212 is connected to a bracket 218, which is in turn slidably coupled with and slidable along a track 220 formed into and along the second segment 178 of the bottom fastener 170. The brackets 214 and 218 may be selectively adjusted to different positions along the tracks 216 and 220, respectively, and may remain in said different positions by friction or another mechanical means known in the art, for instance and without limitation. The illustration of FIG. 4 shows, by way of example, the sliding of the second elongate member 212 along the bottom fastener 170, from a first position (indicated with reference numeral 212) to a second position (indicated by reference numeral 212'); the change in position is provided by the sliding of the corresponding bracket 218 along the corresponding track 220, as indicated by arrow C.

As shown for instance in FIGS. 1 and 2, in some embodiments, such as the present embodiment, at least one of the first and second elongate members 210 and 212 may be mountable over or outside of the top fastener 160, and preferably not engaged, attached, or secured to the top fastener 160. Such configuration may facilitate adjusting the position of the top fastener 160 on one hand, and the first and second elongate members 210 and 212 on the other, with minimal or no interference therebetween, during operation of the spinal traction device 100.

Figure 5:
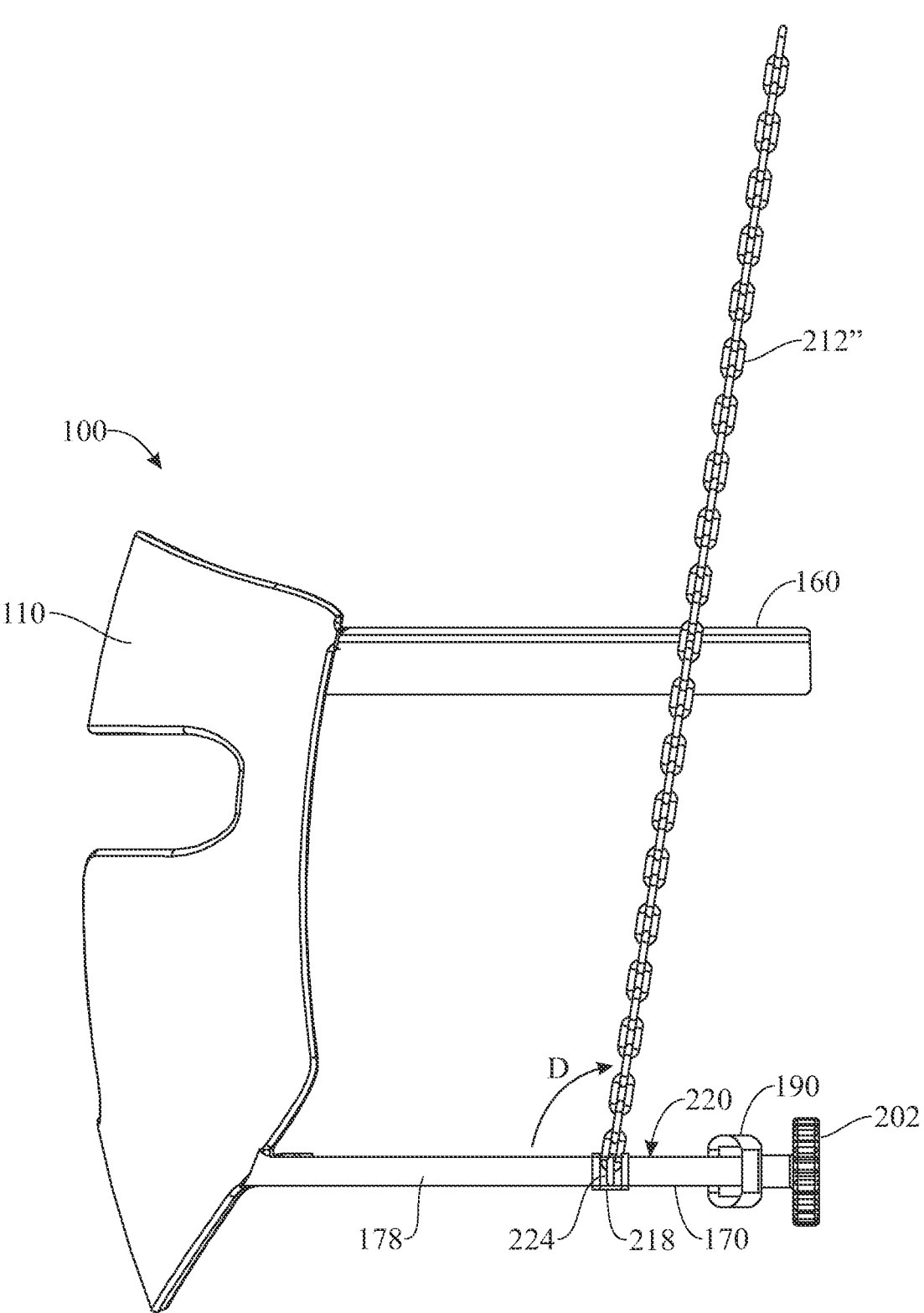
FIG. 5 presents a side elevation view, similar to FIG. 4, showing an angular adjustment of the second elongate member relative to the bottom fastener.

Referring to FIGS. 2 and 5, in some embodiments, at least one of the first and second elongate members 210 and 212 may be reorientable relative to the bottom fastener 170 to vary an angle formed with the bottom fastener 170. For example, as shown in FIG. 2, each one of the first and second elongate members 210 and 212 may be pivotably connected to the respective bracket 214 and 218 by a respective ring 222 and 224, or by another pivotable connection such as a ball joint, pivot pin, etc., which provides an articulated connection between the respective elongate member 210, 212 and the respective bracket 214, 218, the articulated connection enabling a frontward and rearward flexing of the top and bottom fasteners 160, 170 (and thus the head and neck) relative to the first and second elongate members 210 and 212. As shown in FIG. 5, with reference to the second elongate member 212 and as indicated with arrow D, the articulated connection between the second elongate member 212 and the corresponding bracket 218 (e.g., via the ring 224), enables the second elongate member 212 to be tilted or reoriented to vary the angle formed between the second elongate member 212 and section of the bottom fastener 170 at which the bracket 218 is located (e.g., the second segment 178). For example, the second elongate member 212 is shown pivoted or tilted to an oblique position indicated with reference numeral 212". It should be noted that the first elongate member 210 may be similarly repositioned relative to the first segment 176. Such angular repositioning of the first and second elongate members 210 and 212 may facilitate, for instance, sliding the first and second elongate members 210 and 212 along the bottom fastener 170, or temporarily moving the first and second elongate members 210 and 212 out of the way of other elements of the spinal traction device 100 and/or parts of the wearer's head 302, such as the ear 324 (FIG. 3), if needed.

Alternatively or additionally, and preferably additionally, the first and second elongate members 210 and 212 may be torsionable, and/or torsionally connected to the respective bracket 214 and 218, to enable a sideways rotation of the top and bottom fasteners 160, 170 (and thus the head and neck) relative to the first and second elongate members 210 and 212. For example, the depicted first elongate member 210 itself may be twisted or torsioned, and may also be rotated relative to the bottom fastener 170 about a central longitudinal axis of the first elongate member 210. Similarly, the depicted second elongate member 212 itself may be twisted or torsioned, and may also be rotated relative to the bottom fastener 170 about a central longitudinal axis of the second elongate member 212.

In an illustrative method of operation of the spinal traction device 100, and with reference to FIGS. 1, 3 and 6, the spinal traction device 100 may be initially fitted on the wearer's head 302. For this purpose, the knob 202 may be operated to increase the size of the looped, second fastener 170, in some embodiments, such as the present embodiment, such operation may be performed by specifically rotating the knob 202 counterclockwise, i.e. oppositely to arrow A indicated in FIG. 6, as heretofore described. As a result of such operation of the knob 202, the overlapping of the second segment 178 over the first segment 176 of the bottom fastener 170 may be reduced, thereby enlarging the loop formed by the bottom fastener 170 and the front piece 110. Next, the spinal traction device 100 may be slipped over the head 302, by the wearer 300 him or herself or by a medical professional, by initially fitting the enlarged, bottom fastener 170 over and onto the head 302 and downwards towards the neck 318, until the top fastener 160 fits around the top 314 of the head 302 and the front piece 110 is arranged in place relative to the user's face 326, as shown in FIG. 3. In embodiments where the top fastener 160 is elastically or otherwise size-adjustable, the top fastener 160 may automatically adjust against the top 314 of the head 302.

In the mounted position shown in FIG. 3, in some embodiments, one or more openings formed in the front piece 110, such as, but not limited to, the left eye opening 130, right eye opening 132, nose opening 134 and/or mouth opening 136, may be arranged over and in alignment with the left eye, right eye, nose and/or mouth of the wearer, respectively, contributing to user comfort and relaxed breathing. As shown for instance in FIG. 1, in some embodiments, such as the present embodiment, the retainer 190 may be arranged generally opposite (at the back of the device) to the one or more available eye, nose and mouth openings 130, 132, 134, 136 of the front piece 110 (which are present at the front of the device); in such embodiments, a positioning of the retainer 190 in the area of the occiput 320 may be facilitated by simply correctly positioning the one or more available eye, nose and mouth openings 130, 132, 134, 136 over the corresponding eye, nose, or mouth.

With the spinal traction device 100 in the mounted position of FIG. 3, the wearer 300 or medical professional may make any necessary adjustments to the spinal traction device 100. For example, each one of the first and second elongate members 210 and 212, which may be slidably secured to the bottom fastener 170 and extend over or outside of the top fastener 160, may be independently slidably adjusted along the bottom fastener 170 as in the direction of arrow C (FIG. 4) or oppositely to arrow C. Such slidable adjustment of the first and second elongate members 210 and 212 may facilitate positioning said elongate members away from the wearer's ears 324, such that when the elongate members 210, 212 are tensed during operation of the device, the elongate members 210, 212 do not rub or press against the ears 324.

In another adjustment example, each one of the first and second elongate members 210 and 212 may be independently tilted relative to the bottom fastener 170 in the direction of arrow D (FIG. 5) or oppositely to arrow D, as described heretofore. Such angular adjustment may facilitate sliding of the elongate member along the bottom fastener 170, or may place the elongated member out of the way of the front piece 110 or top fastener 160, such as to make final, minor adjustments to the position of the front piece 110 or top fastener 160 relative to the wearer's head 302.

In yet another adjustment example, the knob 202 may be operated as described heretofore with reference to FIGS. 6 and 7 to vary the size of the loop formed by the front piece 110 and the bottom fastener 170, such that the loop is generally smaller than the head 302 and the retainer 190 is snugly yet comfortably placed at the occiput 320 and generally below the inward-oriented or inward surface 322 of the occiput 320 to be able to apply an axial force F1 (FIG. 3) on said inward surface 322.

With the device in place, i.e. with the front piece 110 correctly positioned over the wearer's face 326, the top and bottom fasteners 160, 170 secured to the head 302, the retainer 190 arranged at the wearer's occiput 320, and the first and second elongate members 210, 212 arranged on opposite sides of the head 302, the spinal traction device 100 may be connected to an external traction apparatus (not shown). Specifically, the external apparatus may be engaged with the first and second elongate members 210 and 212, such as at free ends 226 and 228 opposite the brackets 214 and 218, respectively. Next, the subject's head 302 may be oriented or positioned as required, such as, but not limited to, flexed forward, rearward, and/or rotated sideways, or alternatively maintained in a neutral position. As the head 302 is re-positioned, the pivotable connection between each one of the first and second elongate members 210 and 212 and/or the torsionable properties, described heretofore, of the first and second elongate members 210 and 212, allow the elongate members 210, 212 to remain axially positioned despite such repositioning of the head 302 relative to the axial position of the spine. Next, the external apparatus may be operated to exert a pulling force F2 (FIG. 3) on the first and second elongate members 210 and 212, which may be transferred at least partially to the retainer 190, causing the retainer 190 to exert an axial force F1 on the inward surface 322 of the occiput 320. In preferred embodiments, such as the present embodiment, the forces F1 and F2 may be axial (vertical, in the position of FIG. 3) such that said forces F1, F2 do not cause the spine and neck 318 to flex frontward or rearward. In such preferred embodiments, the stretching of the spine may be carried out with the spine in a neutral position, providing increased safety and comfort to the subject, and with the head 302 in various positions as needed.

It should be noted that several factors, particularly if combined, may contribute to a controlled, safe, and maximal transmission of forces from the pulling apparatus (force F2) to the occiput 320 (force F1). Firstly, in embodiments in which the first and second elongate members 210 and 212 are axially non-stretchable, forces may be transferred more efficiently and controlledly. Secondly, having a generally rigid and non-deformable (albeit resizable), bottom fastener 170 may contribute to maximizing force transfer via the bottom fastener 170, from the first and second elongate members 210, 212 to the retainer 190. Thirdly, being able to adjust the bottom fastener 170 such that a loop provided by the bottom fastener 170 and the front piece 110 is generally smaller than the skull, and the bottom fastener 170 thereby may pull axially on the skull, further contributes to increase efficiency and controllability of the force transfer. Furthermore, having the front piece 110 arranged over and softly resting on one or more areas of the face 326, such over one or more of the forehead, temples, cheeks and/or chin, may contribute to stabilizing the front piece 110, particularly in embodiments in which the front piece 110 is generally rigid; by stabilizing the front piece 110 against the wearer's face 326, the bottom fastener 170 (which is preferably fixedly attached to the front piece 110) may be stabilized relative to the head 302, thereby reducing force (energy) loss during the traction procedure or treatment. In addition, having the top fastener 160 snugly secured to the head 302 may further stabilize the bottom fastener 170 relative to the head 302, with a similar effect. In yet another factor, having the first and second elongate members 210 and 212 overlap or extend over the top fastener 160 without being secured or engaged with the top fastener 160 may contribute to maintain the spinal traction device 100 stably positioned on the head 302 during the traction procedure, and to have forces more directly transferred from the pulling first and second elongate members 210 and 212 to the occiput 320 via only the bottom fastener 170 and retainer 190.

Furthermore, in embodiments in which the front piece 110 and bottom fastener 170 are generally rigid, and the bottom fastener 170 is arranged generally spaced-apart from the head 302 (except for the abutting against the occiput 320), pinching of the wearer's face 326 and head during the decompression therapy is minimized, thereby increasing user comfort.

Once the traction procedure has finalized, the spinal traction device 100 may be easily and conveniently removed from the head 302. Specifically, the wearer 300 or medical professional may loosen the knob 202 to sufficiently enlarge the loop formed by the bottom fastener 170 and the front piece 110 so that said loop may slide over and out of the head 302. Next, the spinal traction device 100 may be pulled off the head 302 by consecutively sliding the top fastener 160 and the bottom fastener 170 off the head 302. Once removed from the head 302, the relatively compact, spinal traction device 100 may be easily transported and stored for later use.

Figure 8:
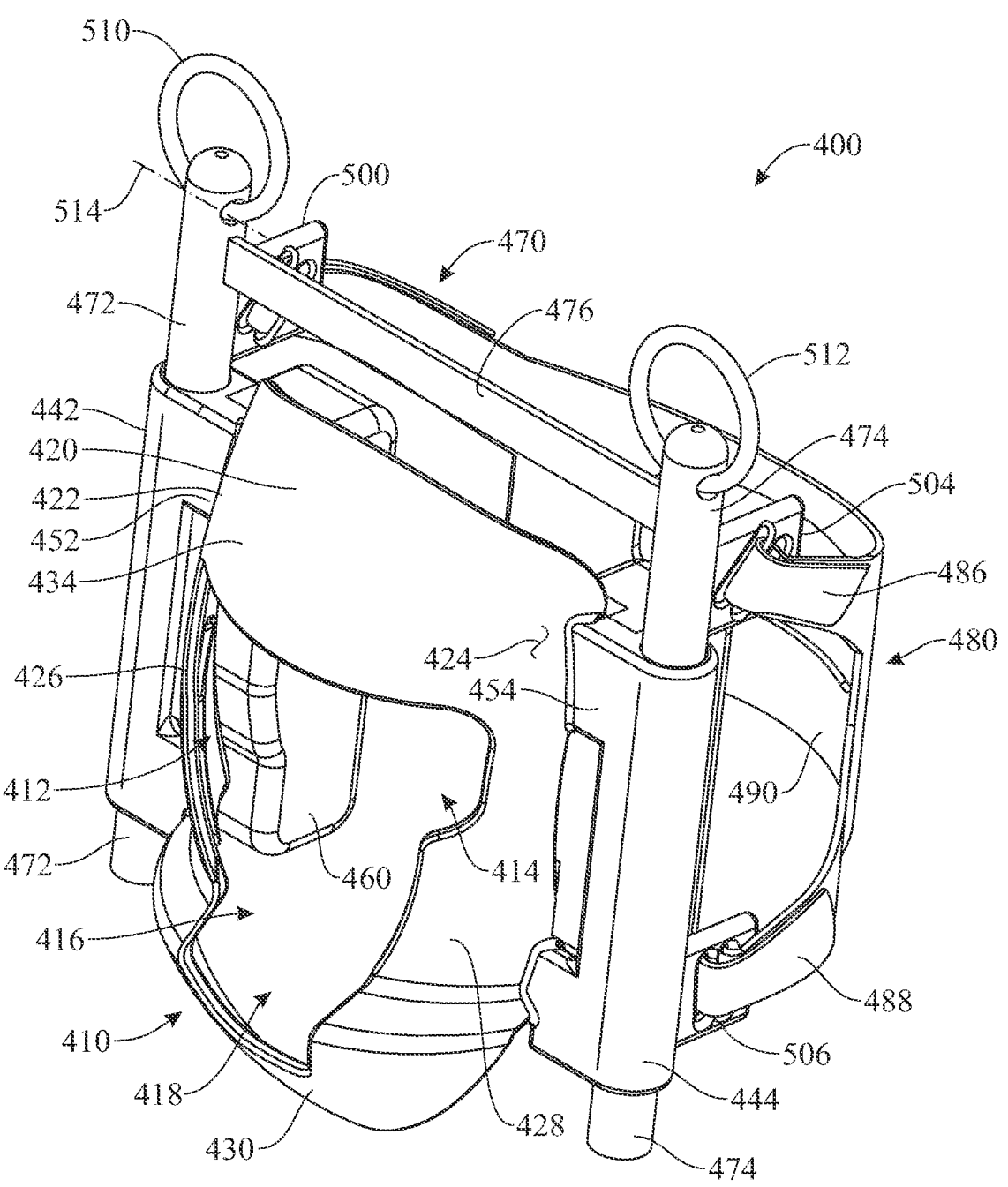
FIG. 8 presents a top, front isometric view of a spinal traction device in accordance with a further embodiment of the present invention.
Figure 9:
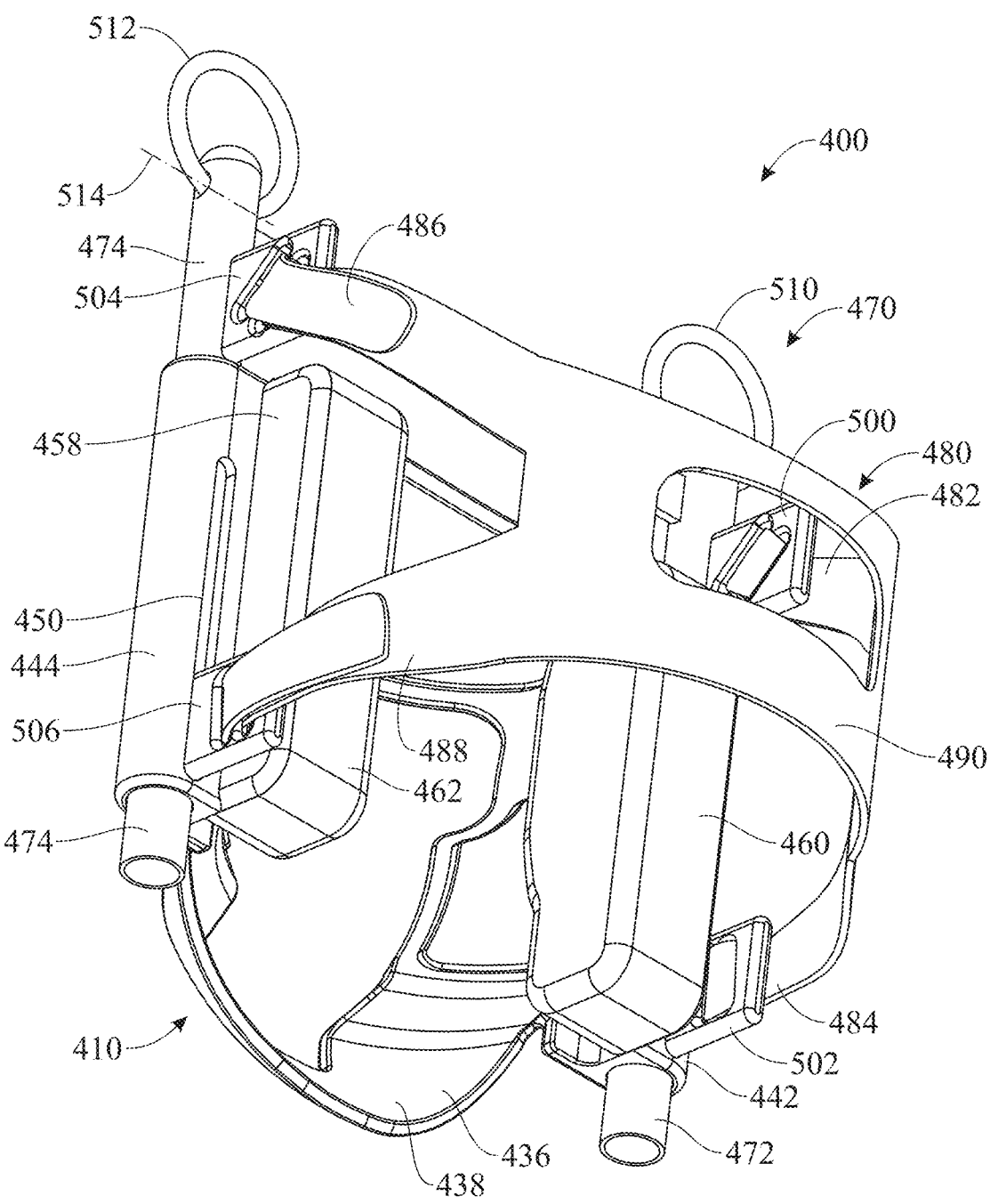
FIG. 9 presents a bottom, rear isometric view of the spinal traction device of FIG. 8.
Figure 12:
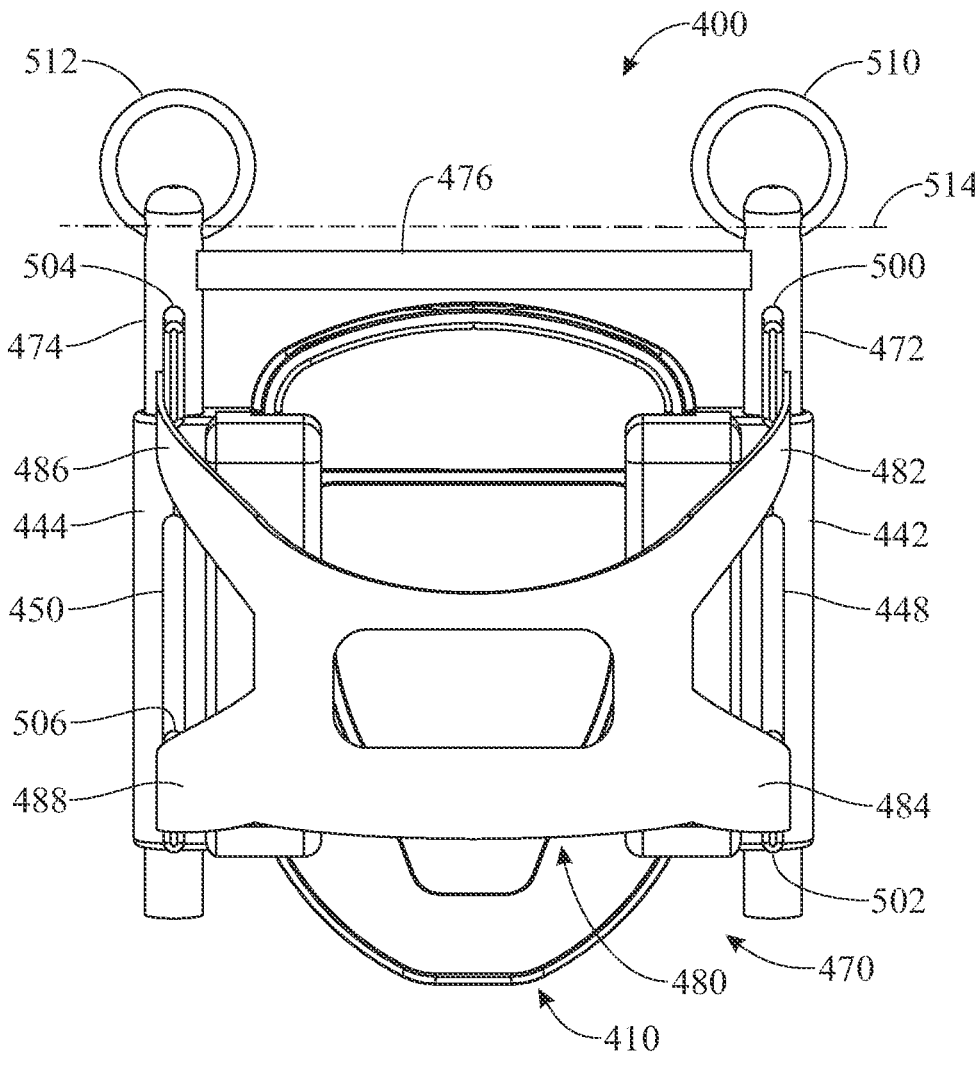
FIG. 12 presents a rear elevation view of the spinal traction device of FIG. 8.
Figure 13:
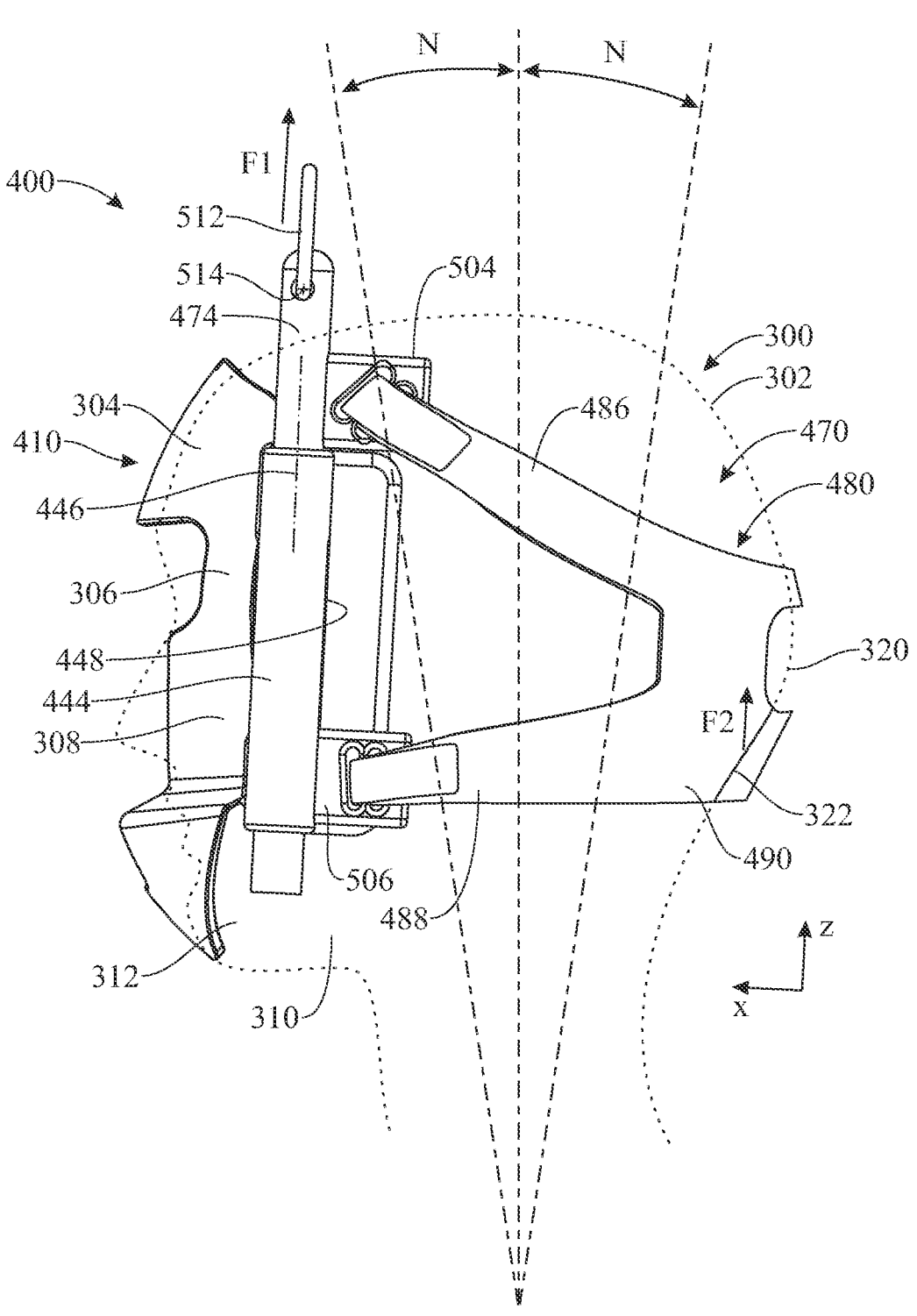
FIG. 13 presents a side elevation view of the spinal traction device of FIG. 8 fitted on a wearer's head, with the fastener assembly slidably arranged in a lower or non-extended, first position relative to the front piece.
Figure 14:
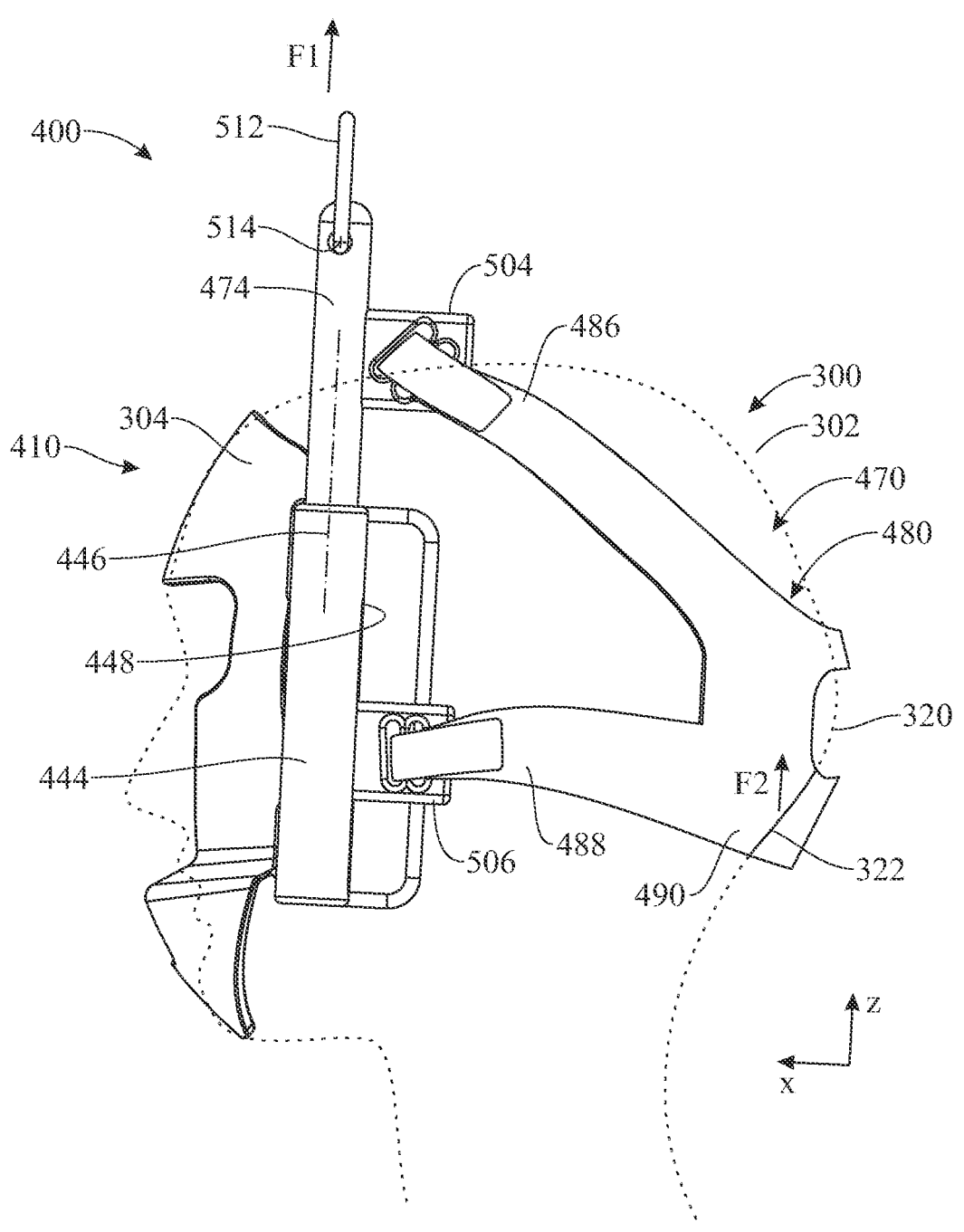
FIG. 14 presents a side elevation view of the spinal traction device, similar to FIG. 13, with the fastener assembly slidably arranged in an upper or extended, second position relative to the front piece.

The illustrations of FIGS. 8-14 show a spinal traction device 400 in accordance with a further embodiment of the present invention. Similarly to the spinal traction device 100 of the previous embodiment, the spinal traction device 400 is mountable on a head 302 (FIGS. 13-14) of a wearer 300 and configured to exert a traction on the head 302. With reference initially to FIGS. 8 and 9, as with the previous embodiment, the spinal traction device 400 includes a front piece 410 and a fastener assembly 470. The front piece 410 is arrangeable in front of the face 326 (FIGS. 13-14) of the wearer 300 to at least partially cover the face 326. In turn, the fastener assembly 470 is attachable to and extendable from the front piece 410 to form a loop together with the front piece 410. The loop formed by the front piece 410 and the fastener assembly 470 is configured to extend around the head 302 of the wearer 300, as shown in FIGS. 13 and 14. The spinal traction device 400 further includes first and second connecting members 510 and 512 carried by the fastener assembly 470. As with the previous embodiment, the first and second connecting members 510 and 512 may be subjected to a traction force applied by a traction device (not shown), and the spinal traction device 400 may be configured to transfer the traction force to the wearer's occiput 320. As will be discussed in greater detail herein-after, the fastener assembly 470 of the present embodiment is slidably attachable to the front piece 410; when attached to the front piece 410, the fastener assembly 470 may slide in an axial direction relative to the front piece 410, thereby minimizing or preventing traction forces being applied by the spinal traction device 400 on the wearer's face 326, such as on the chin 312, during operation of the spinal traction device 400.

Similarly to previous embodiments, the front piece 410 may include one or more of: a left eye opening 412 configured to align with a left eye of the wearer 300, a right eye opening 414 configured to align with a right eye of the wearer 300, a nose opening 416 configured to align with a nose of the wearer 300, and a mouth opening 418 configured to align with a mouth of the wearer 300. In some embodiments, such as the present embodiment, the front piece 410 comprises all of said left eye, right eye, nose, and mouth openings 412, 414, 416, and 418, with the left eye, right eye, nose, and mouth openings 412, 414, 416, and 418 preferably communicated with one another forming a single opening, which may be generally T-shaped, as shown. In some embodiments, similarly to prior embodiments, the front piece 410 may include a top portion 420 configured to align with the wearer's forehead 304, left and right temple portions 422 and 424 configured to align with the wearer's left and right temples 306, respectively, left and right cheek portions 426 and 428 configured to align with the wearer's left and right cheeks 308, respectively, and a bottom portion 430 configured to align with the wearer's chin 312. The top, left temple, right temple, left cheek, right cheek, and bottom portions 420, 422, 424, 426, 428, and 430 may extend continuously from one another and fully encircle the aforementioned single opening formed by the left eye, right eye, nose, and mouth openings 412, 414, 416, and 418.

The front piece 410 may be generally rigid or undeformable. In a non-limiting example, the front piece 410 may be formed by plastics injection molding or 3D-printing. In some embodiments, the front piece 410 may be molded, printed, or otherwise formed in accordance with a human face. For example, in some embodiments, the front piece 410 may be formed to match a specific wearer, i.e., to match the wearer's face 326. For example, the top, left temple, right temple, left cheek, right cheek, and bottom portions 420, 422, 424, 426, 428, and 430 may be shaped and sized to conform to or represent the wearer's forehead 304, temples 306, cheeks 308 and chin 312.

Figure 10:
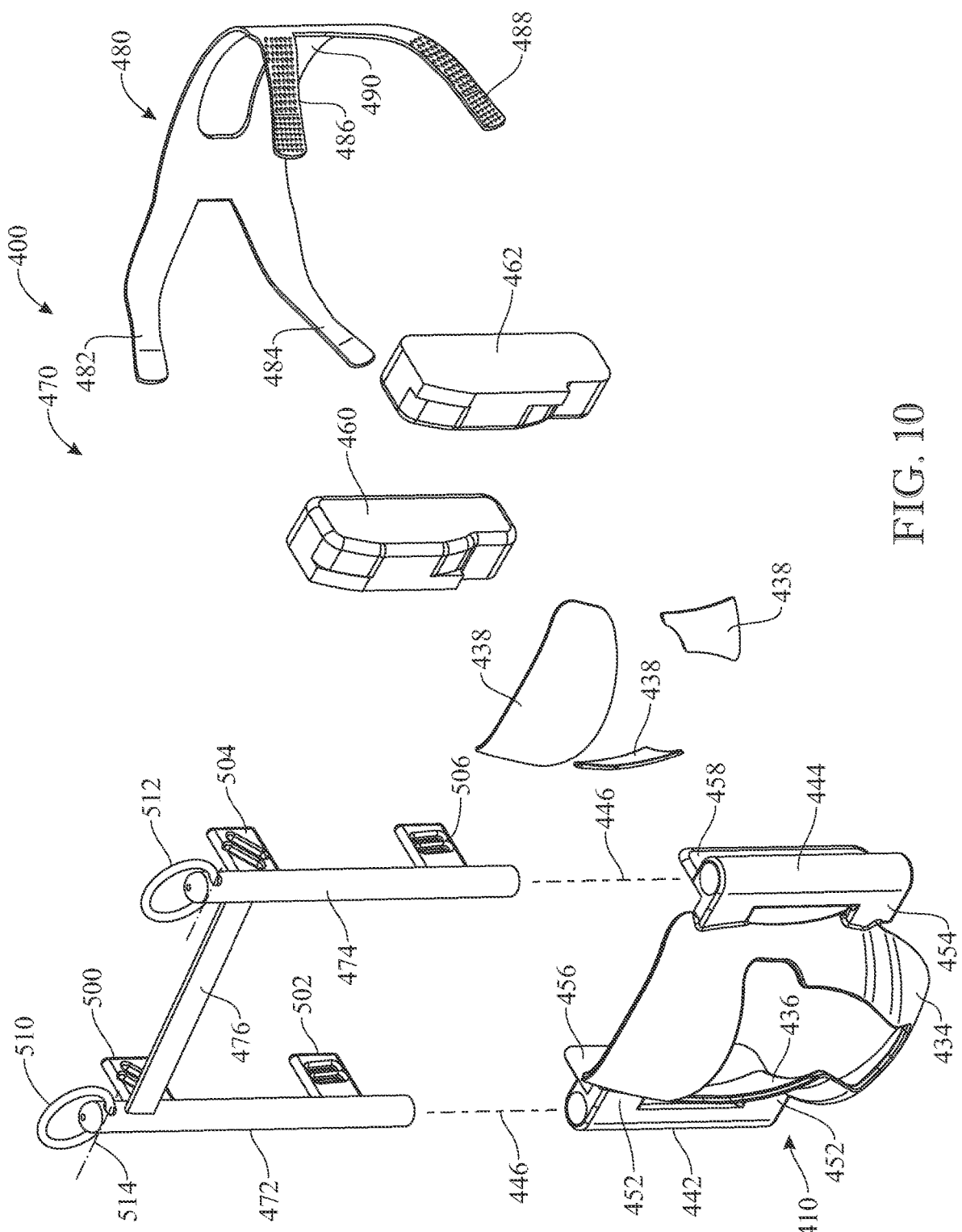
FIG. 10 presents an exploded, top front isometric view of the spinal traction device of FIG. 8.
Figure 11:
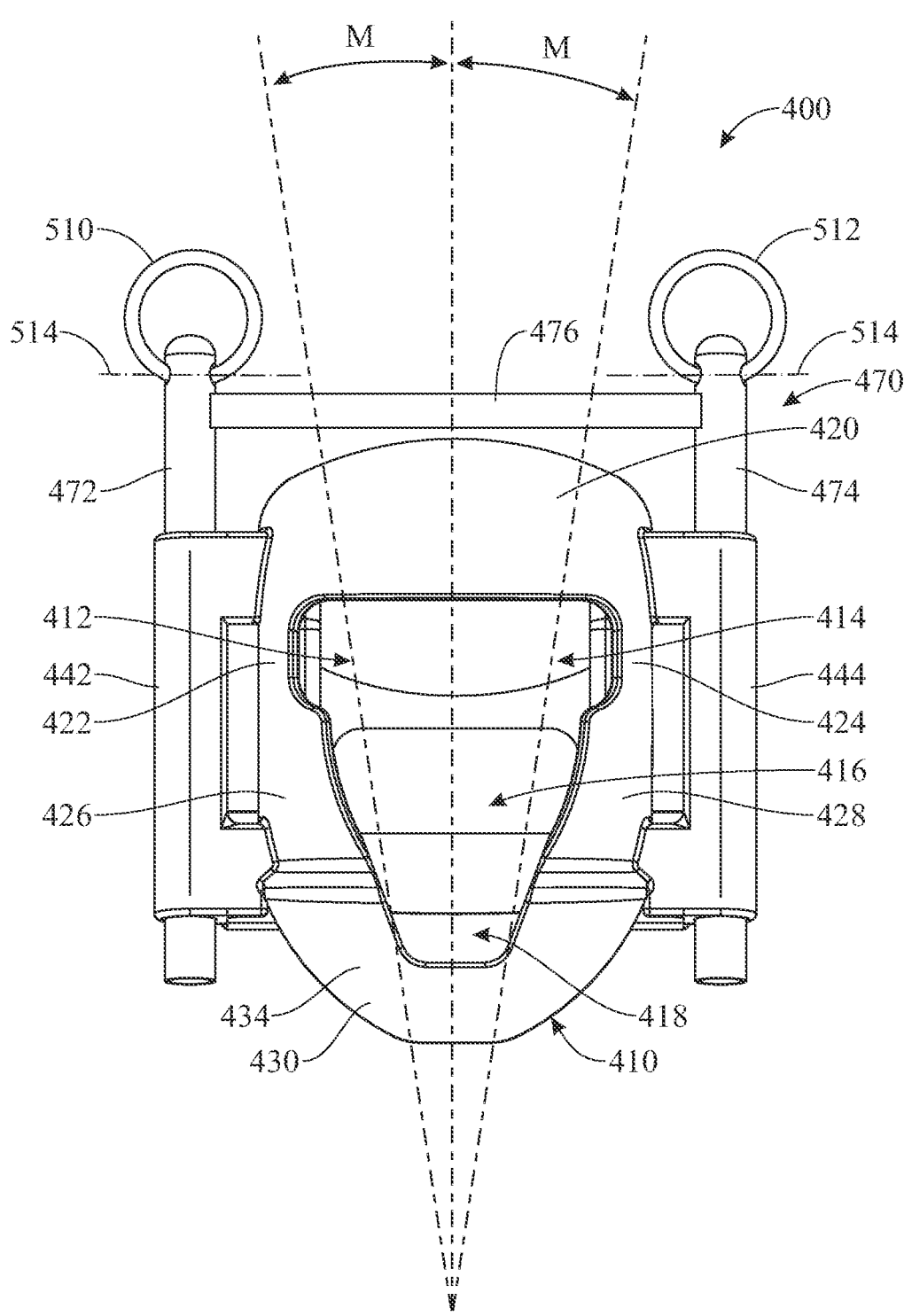
FIG. 11 presents a front elevation view of the spinal traction device of FIG. 8.

With reference to FIG. 10, the front piece 410 may have an outer or front side 434 and an opposite, inner or rear side 436 configured to face away from and towards the wearer's face 326, respectively, during operation of the spinal traction device 400. One or more cushioned linings, layers, or paddings 438 may be provided at the rear side 436 and may dampen a potential contact of the rear side 436 against the wearer's face 326 during operation of the spinal traction device 400 as will be described hereinafter.

As further shown, the front piece 410 may include first and second guide bushings 442 and 444 arranged at opposite, left and right sides of the front piece 410. The first and second guide bushings 442 and 444 may be elongately formed along an axial direction 446, parallel to one another. As shown in FIGS. 9 and 12, a respective slot 448 and 450 may axially extend through the first and second guide bushings 442 and 444, for purposes described hereinafter. The front piece 410 may include first and second transverse flanges 452 and 454 extending laterally outward and carrying the first and second guide bushings 442 and 444 in spaced-apart relationship with left and right sides of the wearer's head. First and second rearward flanges 456 and 458 may extend rearward from the first and second transverse flanges 452 and 454, respectively, and may be provided with a respective cushioned padding 460 and 462, configured to be oriented towards the sides of the wearer's head 302 and to dampen a potential contact of the first and second rearward flanges 456 and 458 against the sides of the wearer's head 302 during operation of the spinal traction device 400.

The fastener assembly 470 comprises rigid, first and second tubes 472 and 474, which are preferably parallel to one another and arranged in the axial direction 446. The first and second tubes 472 and 474 are slidably mountable within the first and second guide bushings 442 and 444 of the front piece 410, enabling the fastener assembly 470 to slidably attach to the front piece 410 such that, when attached to the front piece 410, the fastener assembly 470 may slide in the axial direction 446 relative to the front piece 410. Preferably, the first and second tubes 472 and 474 are relatively snugly (albeit slidably) received within the first and second guide bushings 442 and 444 such that the front piece 410 may maintain a relative front-to-back or left-to-right positioning with respect to the fastener assembly 470 during operation of the device 400, to facilitate or help maintain a correct positioning of the head 302. In some embodiments, the fastener assembly 470 may further include a rigid, connecting bar 476 extending transversely between and rigidly interconnecting the first and second tubes 472 and 474. In some embodiments, the connecting bar 476 and the first and second tubes 472 and 474 may form a generally U-shaped or H-shaped configuration, as shown. The connecting bar 476 synchronizes the axial displacement of the first and second tubes 472 and 474 and provides an increased stability and robustness to the overall assembly formed by the first and second tubes 472 and 474 and the connecting bar 476.

The first and second connecting members 510 and 512, which, in some embodiments, are formed as a pair of rings, may be carried by the first and second tubes 472 and 474, respectively. For instance, as shown, the first and second connecting members 510 and 512 of the present embodiment are specifically provided at top, axial ends of the first and second tubes 472 and 474, respectively. In some embodiments, the first and second connecting members 510 and 512 may be pivotably attached to the fastener assembly 470. Each one of the first and second connecting members 510 and 512 may be pivotable relative to the fastener assembly 470 about a respective rotation axis, the rotation axes arranged in a transverse direction perpendicular to the axial direction. For instance, in the present embodiment, the first and second connecting members 510 and 512 are ring-shaped and pivotably attached to the top axial ends of the first and second tubes 472 and 474 about a same, transverse rotation axis 514.

The fastener assembly 470 may further include a flexible strap assembly or harness 480 attachable to the first and second tubes 472 and 474 and configured to wrap around the back of the head 302 of the wearer 300. The harness 480 may include a top left side strap 482 and a bottom left side strap 484 attachable to opposite, top and bottom ends of the first tube 472, respectively. The harness 480 may further include a top right side strap 486 and a bottom right side strap 488 attachable to opposite, top and bottom ends of the second tube 474, respectively. In some embodiments, the harness 480 may be disconnectably attachable to the first and second tubes 472 and 474. For instance, in the present embodiment, the top left side strap 482 and a bottom left side strap 484 are disconnectably attachable to a first top flange 500 and a first bottom flange 502; in turn, the top right side strap 486 and a bottom right side strap 488 are disconnectably attachable to a second top flange 504 and a second bottom flange 506. The first bottom flange 502 and, in some embodiments, the first top flange 500 may be disconnectably attachable to the first tube 472, such as by a snap fastener, elastic clip fastener, magnetic fastener, or the like; the second bottom flange 506 and, in some embodiments, the second top flange 504 may be disconnectably attachable to the second tube 474.

In some embodiments, the fastener assembly 470 may be size-adjustable. For instance, the harness 480 may be adjustably secured to the first and second tubes 472 and 474 such as by an adjustably-overlapping fastener (e.g., hook and loop fastener) provided at each one of the top left side strap 482, bottom left side strap 484, top right side strap 486 and bottom right side strap 488 engaging with a respective slot formed in the corresponding first top flange 500, first bottom flange 502, second top flange 504, and second bottom flange 506. Alternatively or additionally, the harness 480 may be at least partially constructed of stretchable materials which allow the harness 480 to deform to a larger size or extended configuration, such as to accommodate the head 302, and to be elastically biased towards a smaller size or compressed configuration to adjust against the head 302 once the harness 480 has been fitted over the head 302.

Operation of the spinal traction device 400 is now described with reference primarily to FIGS. 8, 13 and 14. In operation, the spinal traction device 400 may adopt a working configuration similar to that of the spinal traction device 100 of the previous embodiment. In the working configuration, shown in FIGS. 12 and 13, the fastener assembly 470 is attached to and extends from the front piece 410 such that the front piece 410 and fastener assembly 470 form a loop as described heretofore. The spinal traction device 400 is fitted onto the head 302 such that said loop formed by the front piece 410 and the fastener assembly 470 extends about the head 302, with the front piece 410 arranged in front of the face 326 of the wearer 300 and the fastener assembly 470 wrapped around the back of the head 302 of the wearer 300. The left eye, right eye, nose, and mouth openings 412, 414, 416, and 418 (FIG. 8), which form a single opening in this embodiment, are aligned with the wearer's left eye, right eye, nose, and mouth, providing comfort and reassurance to the wearer 300. The first and second transverse flanges 452 and 454 maintain the first and second guide bushings 442 and 444 of the front piece 410 in spaced-apart relationship with the left and right sides of the head 302 of the wearer 300. The cushioned paddings 348, 460, 462 of the front piece 410 are arranged facing the wearer's head 302. The first and second tubes 472 and 474 of the fastener assembly 470 are slidably received within the first and second guide bushings 442 and 444. The first top and bottom flanges 500 and 502 are attached to the first tube 472, with the first bottom flange 502 arranged within the slot 448 of the first tube 472. Similarly, the second top and bottom flanges 504 and 506 are attached to the second tube 474, with the second bottom flange 506 arranged within the slot 448 of the second tube 474. The first and second connecting members 510 and 512 are arranged at opposite sides of the spinal traction device 400, which, in turn, are arranged at opposite left and right sides of the head 302.

In turn, a rear portion 490 of the fastener assembly 470, and more specifically of the harness 480, is arranged adjacent to an inwardly-directed surface 322 of an occiput 320 of the head 302 and is aligned with the inwardly-directed surface 322 in an axial direction of a spine of the wearer 300. The rear portion 490 is also axially aligned with the inwardly-directed surface 322, i.e. is arranged generally behind (below, in the figures) the inwardly-directed surface 322 such that the rear portion 490 is positioned to enable an axially upward pushing of the rear portion 490 on the inwardly-directed surface 322. As with the previous embodiment, an inwardly-directed surface 322 is understood to be a surface of the occiput 320 which is sloped such that the surface has an axial component (i.e. a component in the axial direction z of the wearer's spine) and a front-to-back component (i.e. a component in a front-to-back direction x, generally perpendicular to the axial direction z). It should be noted that the axial direction 446 of the bushings 442, 444 preferably match (is parallel to) the axial direction z of the spine when the wearer's head 302 is placed in a neutral position.

In some embodiments, the spinal traction device 400 may be further positioned such that the first and second tubes 472 and 474 are slidably arranged with respect to the first and second guide bushings 442 and 444 in a first or retracted position in which the first and second tubes 472 and 474 are relatively closer to the wearer's body, as shown in FIG. 13. In this first position, the first and second bottom flanges 502 and 506 may be arranged at or near a bottom end of the respective slots 448 and 450 of the first and second guide bushings 442 and 444, respectively. By means of an external traction device (not shown), a pulling or traction force F1 is controlledly applied on the first and second connecting members 510 and 512 as if to pull the first and second connecting members 'away' from the wearer's body 302. The traction force F1 has an axial component, i.e. a component in axial direction z, and a similar component in the axial direction 446 of the first and second guide bushings 442 and 444; it should be noted that, in embodiments in which direction z and axial direction 446 are parallel, both components may be equal.

As a result of the traction force F1 being exerted on the first and second connecting members 510 and 512, the first and second connecting members 510 and 512 pull axially on the first and second tubes 472 and 474, causing the first and second tubes 472 and 474 and attached flanges 500, 502, 504 and 506 to slide upward relative to the first and second guide bushings 442 and 444. As a result, the flanges 500, 502, 504 and 506 exert an axial pulling or traction force on the harness 480 which causes the rear portion 490 of the harness 480 to abut against and exert a resulting traction force F2 on the inwardly-directed surface 322 of the occiput 320. As a result of the traction force F2, the occiput 320 is gently and controlledly pulled away from the wearer's body to cause a stretching of the wearer's spine.

As mentioned, continued exertion of the traction force F1 on the first and second connecting members 510 and 512 causes the first and second tubes 472 and 474 and attached flanges 500, 502, 504 and 506 to slide upward relative to the first and second guide bushings 442 and 444. Such a sliding movement may be observed in the sequence of FIGS. 13 and 14, where FIG. 13 shows the first and second tubes 472 and 474 and attached flanges 500, 502, 504 and 506 in the aforementioned retracted or first position, and FIG. 14 shows the first and second tubes 472 and 474 and attached flanges 500, 502, 504 and 506 in an advanced, second position farther from the wearer's body. It should be noted that, during this extension sliding movement, the traction force F1 is generally not transmitted to the first and second guide bushings 442 and 444, and thus to the front piece 410, by having the traction force F1 applied on parts which are slidable with respect to the first and second guide bushings 442 and 444 (friction between sliding parts may be considered minimal). In this way, the traction force applied on the first and second connecting members 510 and 512 is generally not transferred to the front piece 410, and the spinal traction device 410 thereby does not pull on the wearer's chin or other areas of the face. This not only provides an increased comfort to the wearer, but also allows the traction to be carried out with the head optionally tilted laterally, as indicated by arrows M in FIG. 11, or frontward or rearward, as indicated by arrows N in FIG. 13. It should be noted that, by having the first and second connecting members 510 and 512 rotatably connected to the fastener assembly 470 about rotation axis 514, exertion of the traction force F1 may be facilitated in different applications where the wearer 300 is positioned differently with respect to the external traction device, by allowing to slightly vary the angle of the traction force F1 with respect to the axial direction 446 while still having the traction force F1 primarily parallel to the axial direction 446.

The spinal traction device disclosed herein may facilitate performing cervical, lumbar, and other spinal decompression therapies with the spine arranged in a neutral position and the head and neck arranged in a neutral position, or in flexed (or extended), rotated and/or other applicable positions. The device provides a means for axially decompressing the neck, unloading the head, neck, and shoulder, and thereby also decompressing the mid back. The invention may be used to carry out a variety of gentle and painless, motion stretching exercises. The device may be easily and conveniently used in a therapeutic setting or at home. The subject may be positioned lying down, face up or face down, or in other positions if needed. In some embodiments, the rigid, non-elastic, non-stretching, non-pliable structure materials of the mask, temporal area flaps, and wrap around head straps fixtures or harness, upon the lower head/skull (occiput area) create a rigid stable loop structure, which in preferred embodiments may be in the shape of a D, which enables for maximum axial distractive force application without any compression upon the TMJ joints and most importantly without any slippage off the head during maximum distractive force applications well above 100-200 lbs.

Since many modifications, variations, and changes in detail can be made to the described preferred embodiments of the invention, it is intended that all matters in the foregoing description and shown in the accompanying drawings be interpreted as illustrative and not in a limiting sense. Furthermore, it is understood that any of the features presented in the embodiments may be integrated into any of the other embodiments unless explicitly stated otherwise. The scope of the invention should be determined by the appended claims and their legal equivalents.

What is claimed is:

1. A spinal traction device, mountable on a head of a wearer and configured to exert a traction on the head of the wearer, comprising:

a rigid front piece, comprising a face mask and first and second guide bushings rigidly connected to the face mask and arranged at opposite, left and right sides of the face mask, respectively;

a fastener assembly, comprising rigid, first and second tubes and a flexible harness, wherein the first and second tubes are slidably mounted within the first and second guide bushings, respectively, and the harness is attachable to the first and second tubes and extendable around a back of the head and is size-adjustable to the head; and first and second connecting members carried by the fastener assembly; wherein the spinal traction device is configured to adopt a working configuration in which:

the face mask is positioned in front of a face of the wearer, and the first and second tubes are slidable relative to the first and second guide bushings along a sliding direction which is parallel to an axial direction of a spine of the wearer, the harness is attached to and extends from the first and second tubes and is wrapped around the back of the head of the wearer such that a rear portion of the fastener assembly is arranged adjacent to an inwardly-directed surface of an occiput of the head and is aligned with the inwardly-directed surface in the axial direction, the first and second connecting members are arranged at opposite sides of the spinal traction device arranged, in turn, at opposite left and right sides of the head, respectively, and a traction force applied on the first and second connecting members, the traction force having an axial component, is transferred by the fastener assembly to said rear portion of the fastener assembly and a resulting traction force having an axial component is applied to said inwardly-directed surface of the occiput of the head by said rear portion of the fastener assembly abutting against the inwardly-directed surface of the occiput.

2. The spinal traction device of claim 1, wherein the face mask comprises at least one of a left eye opening configured to align with a left eye of the wearer, a right eye opening configured to align with a right eye of the wearer, a nose opening configured to align with a nose of the wearer, and a mouth opening configured to align with a mouth of the wearer when the spinal traction device is arranged in the working configuration.

3. The spinal traction device of claim 2, wherein the face mask comprises all of said left eye, right eye, nose, and mouth openings, wherein the left eye, right eye, nose, and mouth openings are communicated with one another forming a single opening, the face mask further comprising a top portion configured to align with a forehead of the wearer, left and right temple portions configured to align with left and right temples of the wearer, respectively, left and right cheek portions configured to align with left and right cheeks of the wearer, respectively, and a bottom portion configured to align with a chin of the wearer, wherein the top, left temple, right temple, left cheek, right cheek and bottom portions extend continuously from one another and fully encircle said single opening.

4. The spinal traction device of claim 1, wherein the face mask is formed in accordance with the wearer's face.

5. The spinal traction device of claim 1, wherein the fastener assembly further comprises a rigid, connecting bar extending transversely between and rigidly interconnecting the first and second tubes.

6. The spinal traction device of claim 1, wherein the first and second connecting members are carried by the first and second tubes, respectively.

7. The spinal traction device of claim 6, wherein the first and second connecting members are provided at axial ends of the first and second tubes, respectively.

8. The spinal traction device of claim 1, wherein the flexible harness comprises top and bottom left side straps attachable to opposite, top and bottom ends of the first tube, respectively, and top and bottom right side straps attachable to opposite, top and bottom ends of the second tube, respectively.

9. The spinal traction device of claim 1, wherein the front piece comprises first and second side flanges comprising a respective cushioned inner side, wherein, in the working configuration, the respective cushioned inner sides face left and right sides of the head of the wearer and the first and second side flanges maintain the first and second guide bushings of the front piece in spaced-apart relationship with the left and right sides of the head of the wearer.

10. The spinal traction device of claim 1, wherein the first and second connecting members are pivotably attached to the fastener assembly.

11. The spinal traction device of claim 10, wherein each one of the first and second connecting members is pivotable relative to the fastener assembly about a respective rotation axis, the rotation axes arranged in a transverse direction perpendicular to the axial direction.

12. The spinal traction device of claim 1, wherein each one of the first and second connecting members comprises a respective ring.

13. The spinal traction device of claim 12, wherein the respective rings of the first and second connecting members are pivotably attached to the fastener assembly.

\*    \*    \*    \*    \*